United States Patent [19]
Papakostopoulos

[11] Patent Number: 5,720,298
[45] Date of Patent: Feb. 24, 1998

[54] ELECTROPHYSIOLOCIAL DATA COLLECTION SYSTEM

[76] Inventor: Demetrius Papakostopoulos, 41 Northumberland Road, Redland, Bristol, United Kingdom, BS6 7BA

[21] Appl. No.: 640,742

[22] PCT Filed: Sep. 15, 1995

[86] PCT No.: PCT/GB95/02172

§ 371 Date: Jul. 31, 1996

§ 102(e) Date: Jul. 31, 1996

[87] PCT Pub. No.: WO96/08997

PCT Pub. Date: Mar. 28, 1996

[30] Foreign Application Priority Data

Sep. 19, 1994 [GB] United Kingdom .................. 9418872

[51] Int. Cl.⁶ .......................................... A61B 13/00
[52] U.S. Cl. ............................................ 128/745; 128/746
[58] Field of Search .................................. 128/745–746

[56] References Cited

U.S. PATENT DOCUMENTS

| | | | |
|---|---|---|---|
| 4,955,389 | 9/1990 | Schneider | 128/745 X |
| 5,422,690 | 6/1995 | Rothberg et al. | 128/745 X |
| 5,507,291 | 4/1996 | Stirbl et al. | 128/745 X |
| 5,617,872 | 4/1997 | Scinto et al. | 128/745 |

*Primary Examiner*—Francis Jaworski
*Attorney, Agent, or Firm*—Larson & Taylor

[57] ABSTRACT

An electrophysiological data collection system is described which includes a flash lamp for transmitting a stimulus to a subject, electrodes for deriving electrophysiologic data from the subject, an amplifier for processing the data, a contrast sensor for monitoring the flash lamp, an illumination sensor for measuring ambient light, and a connection box for controlling the amplifier according to the outputs of the contrast sensor and illumination sensor.

15 Claims, 1 Drawing Sheet

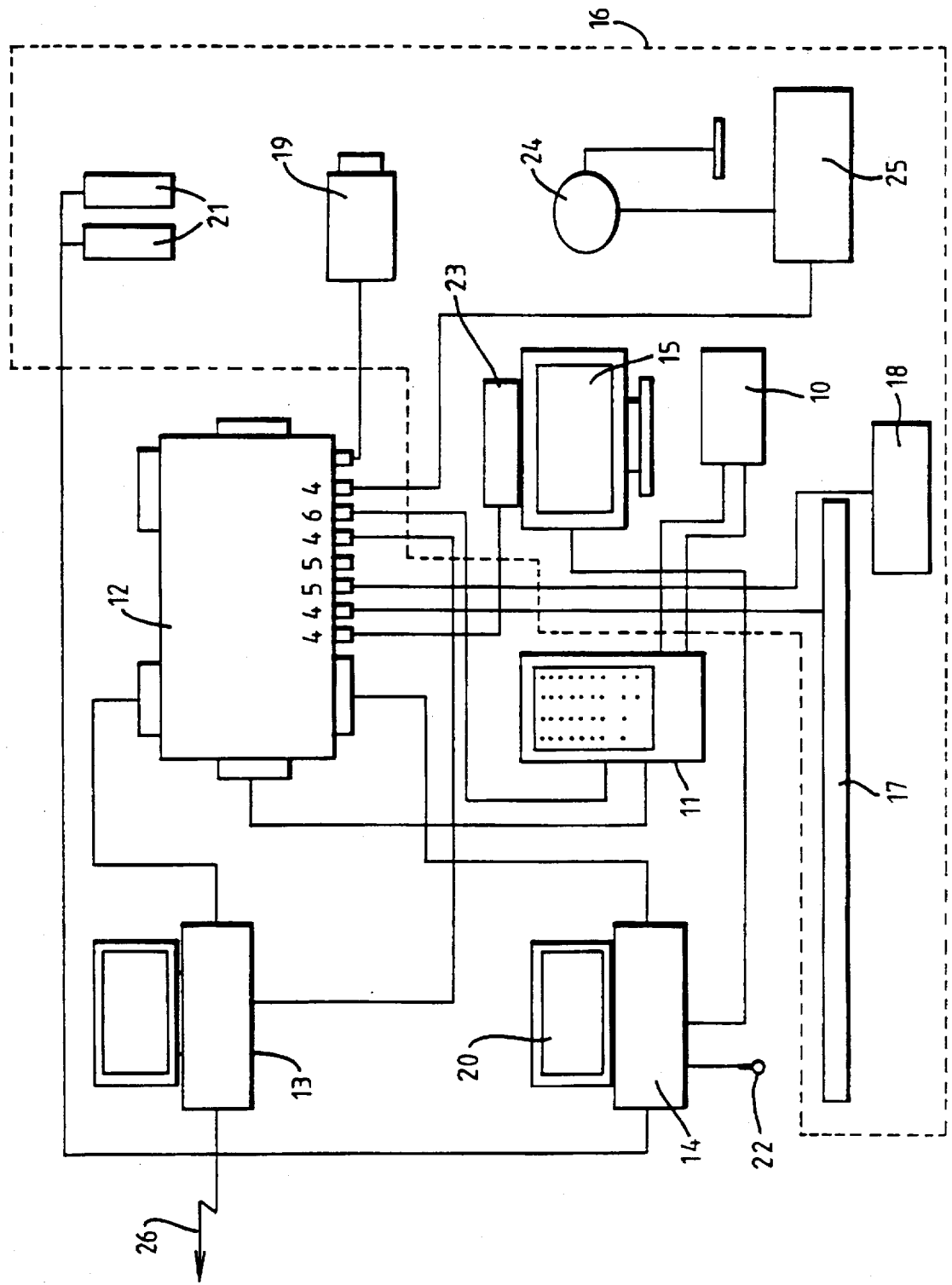

# ELECTROPHYSIOLOCIAL DATA COLLECTION SYSTEM

BACKGROUND OF THE INVENTION

1. Field of the Invention The present invention relates to a system, which collects data corresponding to electrophysiological responses to appropriate stimulation such as sound, touch or visual stimulation. Such a system is particularly, but not exclusively, useful in the diagnosis of diseases on the basis of the data collected.

2. Summary of the Prior Art

It is well established that different stimuli will produce different electrophysiological responses in a subject, and variations in those responses from one subject to another can be used in the diagnosis, prognosis and management of diseases. However, existing attempts to make use of such electrophysiological responses have been carried out in an ad hoc way. A specialist may set up means for presenting different stimuli to a subject, and data corresponding to the electrophysiological responses of the subject may then be recorded. The specialist uses his or her expertise and experience to interpret the data derived from those responses.

However, variations in the conditions under which the subject experienced the stimulus cause variations in the results obtained. The specialist may be able to compensate for this on the basis of his or her own knowledge, when he or she interprets the data, but this makes it very difficult to compare a diagnosis obtained by one specialist with those obtained by another. Moreover, the tests carried out on the subject must be controlled and interpreted by the specialist, so that the tests cannot be carried out by the inexperienced. As a result, the costs of such tests are high.

SUMMARY OF THE INVENTION

The present invention seeks to overcome these problems by providing an electrophysiological data collection system, in which the conditions under which the subject is exposed to the stimulation are controlled to permit standardisation to be achieved.

In order to achieve such standardisation, one or more of the following three features must be present in the system: firstly, means for monitoring, and preferably controlling, the ambient light in the vicinity of the subject, so that tests can be carried out under standardised ambient light conditions, or at least being prevented from being carried out if the ambient light levels do not fall within desired parameters: secondly, means for monitoring, and preferably controlling, the stimulus which the subject experiences, to ensure that the stimulus has predetermined characteristics, or at least characteristics within a given range, and thirdly, means for varying the processing of the electrophysiological data from the subject in dependence on the stimulus, which itself will vary in dependence on the electrodiagnostic test being carried out on the subject.

The present invention is applicable to tests involving many different types of stimulation. It has been developed particularly for visual stimulation, but may be applied to auditory, somatosensory, cognative or autonomic tests. In each case, it is desirable that all conditions be controlled, since an auditory event occurring at the time of the visual stimulus could affect the results obtained from a test based on that visual stimulus.

Ideally, the system would ensure that the conditions under which the tests were carried out were entirely uniform. In some cases, however, variation may arise, not from the environment, the stimulus or the subject, but from unequal amplification of the many amplifiers used simultaneously to amplify the signals from the subject. The system therefore preferably has means for compensating for any such variations to equalise the behaviour of all amplifiers.

Thus, a subject may be placed in a suitable location, such as a windowless room, and the ambient light controlled on the basis of detection of that light by suitable sensors. Once the operator has input the diagnosis test to be carried out, the system is configured to adapt it to the signals that are expected to result from that test, and then the subject is exposed to appropriate stimulation corresponding to the desired diagnostic text. The electrophysiological signals generated by the subject may then be stored for analysis.

When a test is carried out on the basis of visual stimulation, for example, it is important that the subject is looking in the correct direction at the time of the test. For example, if the visual stimulation is presented on a monitor screen, and the subject's eyes are not focused on that screen at the time of the stimulation, an unsuitable test result may be obtained. Therefore, it is desirable that the operator has means for checking that the subject is in the correct position, before administering the visual stimulation. Therefore, it is preferable that a camera is provided which enables the subject to be viewed. If the room in which the subject is located is to be dark during one or more of these tests, that camera may operate in the infra-red.

As was mentioned above, the visual stimulation may be provided by way of a monitor screen. The contrast, and possibly brightness, of that screen will then need to be sensed, and preferably controlled, to ensure that the subject receives the correct stimulation. Alternatively, or in addition, the visual stimulus may be by way of a flash of light, and the intensity, duration, colour and flash frequency may all need to be monitored, and preferably controlled, in order to ensure that the subject receives the correct stimulus. Similar adjustments are possible for auditory, somatosensory, cognative and autonomic recordings.

As was mentioned above, it is necessary to adapt the processing of the electrophysiological data from the subject to the test being carried out. Different stimuli will produce different signals, and a rapidly changing signal will need to be processed differently from a slowly changing one. Hence, the processing circuitry needs to be adapted to the test initiated by the operator.

The present invention may be applicable to many different electrodiagnostic techniques. For example, it may be applied to electrooculography, electroretinography, visual evoked and event related potentials, steady state potentials, somatosensory evoked and event related potentials, electromyography, electroencephalography, or autonomic functions (ECG, plethysmography, respiration, etc).

BRIEF DESCRIPTION OF THE DRAWINGS

An embodiment of the present invention will now be described in detail, by way of example, with reference to the accompanying drawing in which the sole FIGURE is a schematic diagram of an electrophysiological data collection system according to an embodiment of the present invention.

DETAILED DESCRIPTION

In order to obtain electrophysiological data from a subject who is to experience visual stimulation, electrodes 10 are placed at suitable positions on the subject's body (not shown), and these electrodes generate electrical signals which vary in dependency on the stimulation which the subject experiences. The signals from the electrodes 10 are passed via an amplifier unit 11 to a connection box 12, and from that connection box 12 to a data collection computer 13.

In order to generate the visual stimulus, an operator controls a stimulation computer 14 to display the visual stimulus on a stimulation monitor screen 15 positioned in the line of sight of the subject, the particular stimulation being displayed on the screen varying in dependence on the particular electrodiagnostic test to be carried out on the subject. Moreover, the electrophysiological signals generated at the electrodes 10 by the subject will vary in their characteristics depending on the stimulation experienced by the subject, and it is necessary for the amplification of those signals by the amplifier unit 11 to vary in dependency on the test being carried out. For example, if the electrodes generate rapidly varying signals, the processing of those signals by the amplifier unit 10 may need to differ from that provided by the amplifier unit 11 if the signals are slowly varying. For this reason, the stimulation computer 14 not only generates a signal to the stimulation monitor screen 15, to provide the visual stimulation, but also passes a signal to the connection box 12, which then controls the amplifier unit 11 in dependence on the type of test.

When administering the test, it is important that the ambient light conditions are uniform, if uniform results are to be obtained. Therefore, the subject will normally be located in a windowless room indicated schematically at 16, and the lights 17 in that room controlled via the connection box 12 so that the ambient illumination in the room 16 is satisfactory to enable the appropriate test to be carried out. To ensure that the ambient illumination is satisfactory, illumination sensors 18 are also connected to the connection box 12, which detect the ambient light.

It is also necessary to ensure that the subject is looking in the correct direction at the time of the test. For example, the subject's eyes may need to be focused on the stimulation monitor screen 15, or possibly the subject needs to look away therefrom. Therefore, it is preferable that a camera 19 be provided directed towards the position of the subject within the room 16, the camera 19 then providing video signals which may be displayed on the monitor screen 20 of the stimulation computer 14, so that the operator has an immediate visual indication of the actions of the eyes of the subject. The operator may therefore control the stimulation computer to ensure that the appropriate visual stimulus is given to the subject only when the subject is looking in the correct direction for the test to be carried out. It may therefore be necessary for the operator to give instructions to the subject, and speakers 21 may be provided in the room 16, connected to the stimulation computer 14, and a microphone 22 be provided at the stimulation computer 14, thereby permitting instructions from the operator to be passed to the subject.

Even minor variations in the brightness and/or contrast of the display on the stimulation monitor screen 15 may affect the results of the test. Therefore, it is preferable that a contrast sensor 23 be provided connected to the stimulation monitor screen 15, supplying signals to the connection box 12. These may be then used to prevent the test being carried out if the contrast is not satisfactory, or even to enable the connection box 12 to control the stimulation monitor screen 15, to achieve the desired levels of brightness and contrast.

It may also be necessary, for some tests, for the subject to be exposed to flashes of light, and therefore a flash lamp 24 may be provided in the room 16, controlled by a control unit 25 connected to the connection box 12.

Thus, when the operator wishes to carry out one or more tests on a subject, the electrodes 10 are placed on the subject, and the operator signals via the stimulation computer that the test is to be carried out. The connection box 12 then checks the operating status of the amplifier unit 11, the camera 19, the data collection computer 13, the lights 17 and illumination sensors 18, in order to ensure that all are operating correctly. Next, when the operator signals via the stimulation computer that a particular test is to be carried out, the connection box 12 then controls the amplifier unit 11 to achieve the required processing of the expected signals from the electrodes 10, and then indicates to the operator that the test may be commenced. The operator monitors the subject via the camera 19 until the subject's eyes are in the correct position and then triggers a particular visual stimulation. The appropriate stimulation is then generated via the monitor screen 15 and/or the flash light 24.

If the operator sees via the camera 19 that the subject's eyes are not in the correct position, no test is carried out. Moreover, if the contrast sensor 23 and/or the illumination sensors 18 indicate that appropriate light levels have not been achieved by the lights 17 or the monitor screen 15, the test results may be rejected. Data collection may therefore be automatically suspended, and a warning given to the operator, if the light parameters deviate from pre-set values, or outside predetermined ranges. If the patient's eyes are not in the correct position (the appropriate degree of gaze fixation is not maintained by the subject), then the operator may also suspend data collection. The latter feature is particularly important if the present invention is applied to diagnosis carried out on young infants, children, or uncooperative subjects such as those with neurological or psychiatric diseases.

It can be seen that, because the system of the present invention maintains constant conditions, or at least provides data collection to be suspended on the basis of sensor signals and/or relatively simple operator information (e.g. that from the camera 19), the system of the present invention may be operated by a relatively inexperienced operator, and still enable satisfactory data to be collected from the subject. The fact that the conditions are controlled also reduces the risk of inaccurate data collection, and so reduces the time of electrodiagnosis. The system may thus be operated by non-specialised staff.

The data collection computer 13 will contain appropriate programs for analysing the data collected. For example, the data may be processed by averaging, scoring, frequency domain analysis, single-trial analysis, component extraction, mapping of phase, amplitude and time characteristics of components, etc. Moreover, the data collection computer 13 may be connected via a telecommunications network 26 to other sites where similar tests are being carried out, or to a central data collection point connected to many such sites. In this way, more advanced data processing, or centralised data collection analysis, can be carried out using the present invention.

Many different tests can be carried out using the system of this embodiment. For example, electrooculography, electroretinography, visual evoked and event related potentials, steady state potentials, somatosensory evoked and event related potentials, electromyography, electroencephalography, or autonomic functions (ECG, plethysmography, respiration, etc) may be carried out. These tests enable many different diseases to be diagnosed, such as Parkinsonism, developmental and learning disabilities in children, and vascular diseases of the eye.

I claim:

1. An electrophysiological data collection system comprising:

stimulus means for transmitting a stimulus to a subject;

measurement means, including electrodes for attachment to the subject, for deriving electrophysiological data from the subject;

processing means for processing said data to produce output data;

first monitoring means for monitoring said stimulus;

second monitoring means for monitoring at least one ambient condition;

control means for controlling said processing means according to an output of said first and second monitoring means; and means for monitoring the position of the subject and verifying that said position is suitable for the subject to be examined.

2. An electrophysiological data collection system according to claim 1 further comprising ambience means for controlling said at least one monitored ambient condition, said control means being arranged to control said ambience means.

3. An electrophysiological data collection system according to claim 1 in which the control means is arranged to interrupt said derivation and processing of the data when said at least one monitored ambient condition is outside a pre-determined operating range.

4. An electrophysiological device according to claim 1, in which the control means is arranged to control the stimulus means and thereby control the stimulus.

5. An electrophysiological data collection system according to claim 1 in which said stimulus is visual, and said at least one ambient condition includes the ambient lighting level.

6. An electrophysiological data collection system according to claim 5 in which said stimulus means include a monitor screen, and said control means are arranged to monitor the contrast and/or brightness of the screen.

7. An electrophysiological data collection system according to claim 1 in which the processing means includes a plurality of amplifiers and said control means is arranged to control the amplifiers.

8. An electrophysiological data collection system according to claim 1 wherein the system is configurable to perform one of plurality of electrophysiological tests using different stimuli on a subject.

9. An electrophysiological data collection system according to claim 1 further comprising means for transmitting the output data produced by said processing means to other non-local sites where electrophysiological tests are being carried out.

10. A method of collecting electrophysiological data from a subject comprising the steps of:

transmitting a stimulus to a subject;

deriving electrophysiological data from the subject using electrodes attached to the subject;

monitoring said stimulus and at least one ambient condition;

monitoring the position of the subject and verifying that said position is suitable for the subject to be examined; and processing said electrophysiological data in accordance with said monitored stimulus and said at least one monitored ambient condition.

11. A method according to claim 10 further comprising the step of controlling said at least one monitored ambient condition.

12. A method according to claim 11 further comprising the step of controlling the level of the stimulus.

13. A method of collecting electrophysiological data for a subject comprising:

(i) providing an electrophysiological data collection system having stimulus means for transmitting a stimulus to a subject, the electrophysiological data collection system having;

measurement means, including electrodes for attachment to the subject, for deriving electrophysiological data from the subject;

processing means for processing said data;

first monitoring means for monitoring said stimulus;

second monitoring means for monitoring at least one ambient condition;

third monitoring means for monitoring the position of the subject and verifying that said position is suitable for the subject to be examined; and control means for controlling said processing means according to an output of said first and second monitoring means, (ii) transmitting a stimulus to the subject; and (iii) collecting said electrophysiological data using said electrophysiological data collection system.

14. An electrophysiological data collection system according to claim 1 further comprising means for transmitting data to a non-local central data collection point.

15. An electrophysiological data collection system according to claim 1 wherein the system is conformable to perform one of a plurality of tests using the same stimuli to measure different electrophysiological conditions.

* * * * *